US00PP31524P2

(12) United States Plant Patent
Wheeler et al.

(10) Patent No.: US PP31,524 P2
(45) Date of Patent: Mar. 10, 2020

(54) BLUEBERRY PLANT NAMED 'BB06-343MI-16'

(50) Latin Name: *Vaccinium corymbosum*
Varietal Denomination: BB06-343MI-16

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/350,521

(22) Filed: Nov. 27, 2018

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — King IP Law; Joshua King

(57) ABSTRACT

'BB06-343MI-16' is a new and distinct high chill tetraploid Northern highbush blueberry (*Vaccinium*) variety. 'BB06-343MI-16' is characterized as having large fruit, medium blue in color, and is very firm with a very small and dry pedicel scar. The fruit is well exposed on a vigorous medium upright bush. Along with a small sized crown, a loose fruit cluster, concentrated ripening, and very firm fruit that is easily detachable, the variety displays characteristics suitable for mechanical harvest. Berries of 'BB06-343MI-16' have very good flavor, a balance of sweetness and acidity and is very juicy with a crunchy texture.

5 Drawing Sheets

Latin name: *Vaccinium corymbosum.*
Common name: Blueberry.
Cultivar name: 'BB06-343MI-16'.

BACKGROUND AND SUMMARY

Blueberries are a well-known fruit enjoyed by many throughout the world. One example of an existing commercial blueberry variety is 'Duke', unpatented. Another example of an existing, patented blueberry variety is 'Draper', U.S. Plant Pat. No. 15,103.

Comparing 'BB06-343MI-16' to 'Duke', the bush habit of 'BB06-343MI-16' is more upright than 'Duke', and the fruit of 'BB06-343MI-16' is much firmer and slightly darker in color than the fruit of 'Duke'.

Comparing 'BB06-343MI-16' to 'Draper', the bush habit of 'BB06-343MI-16' is more upright than 'Draper', the berry size and weight of 'BB06-343MI-16' are less than for 'Draper', the time of maturity of 'BB06-343MI-16' is 10 days earlier, the berry firmness of 'BB06-343MI-16' is much better and the berry height of 'BB06-343MI-16' is less than 'Draper'.

The present cultivar, 'BB06-343MI-16', provides one or more advantages compared to these and/or other blueberry varieties.

BRIEF DESCRIPTION OF THE PHOTOGRAPHS

DETAILED DESCRIPTION

Figure 1:
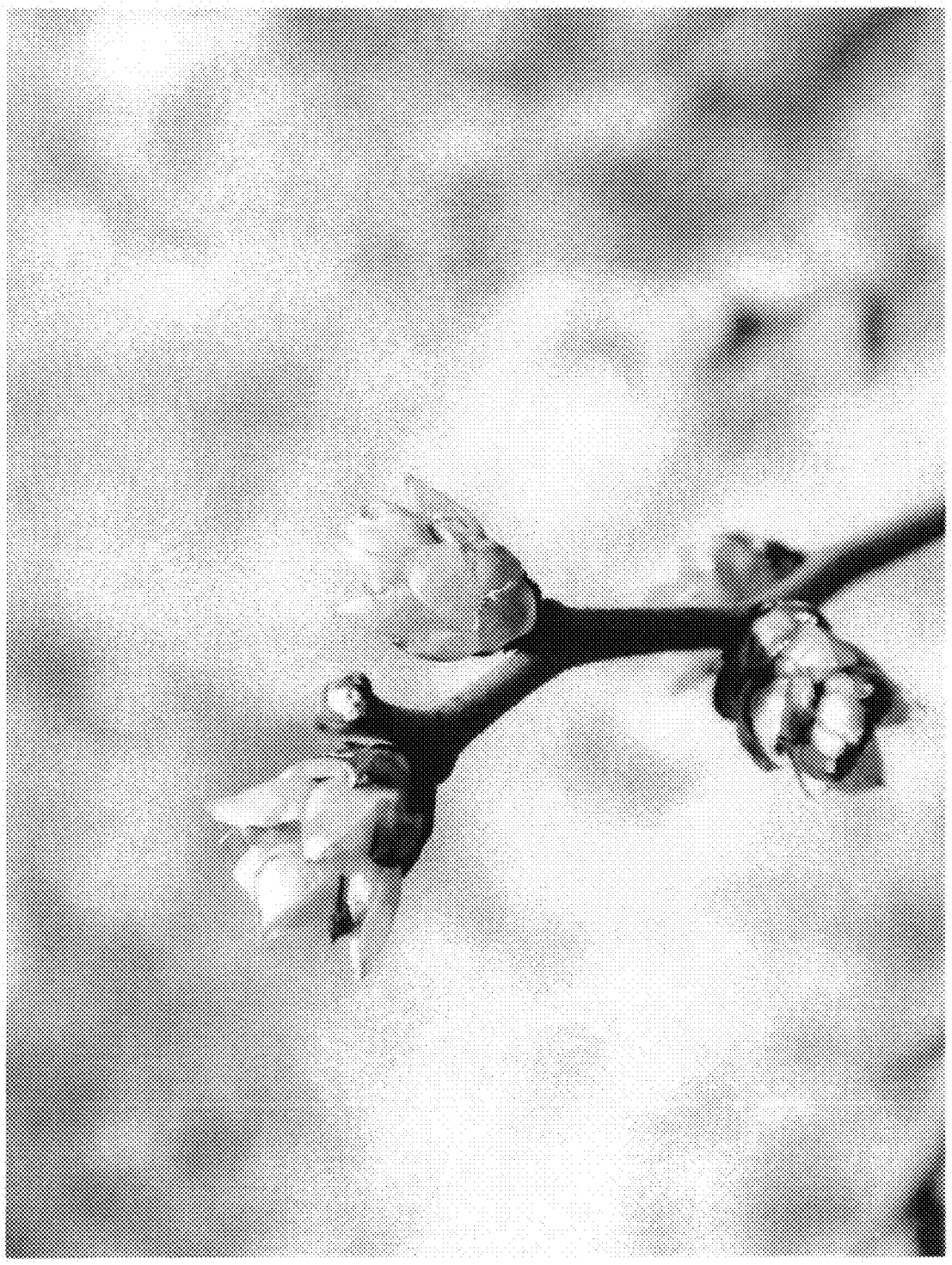
FIG. 1 is a close-up photograph of 'BB06-343MI-16' taken in Mid-April, 2018, in Grand Junction, Mich., and shows emerging flower buds, their shape and color, also the fruiting wood early spring color.
Figure 2:
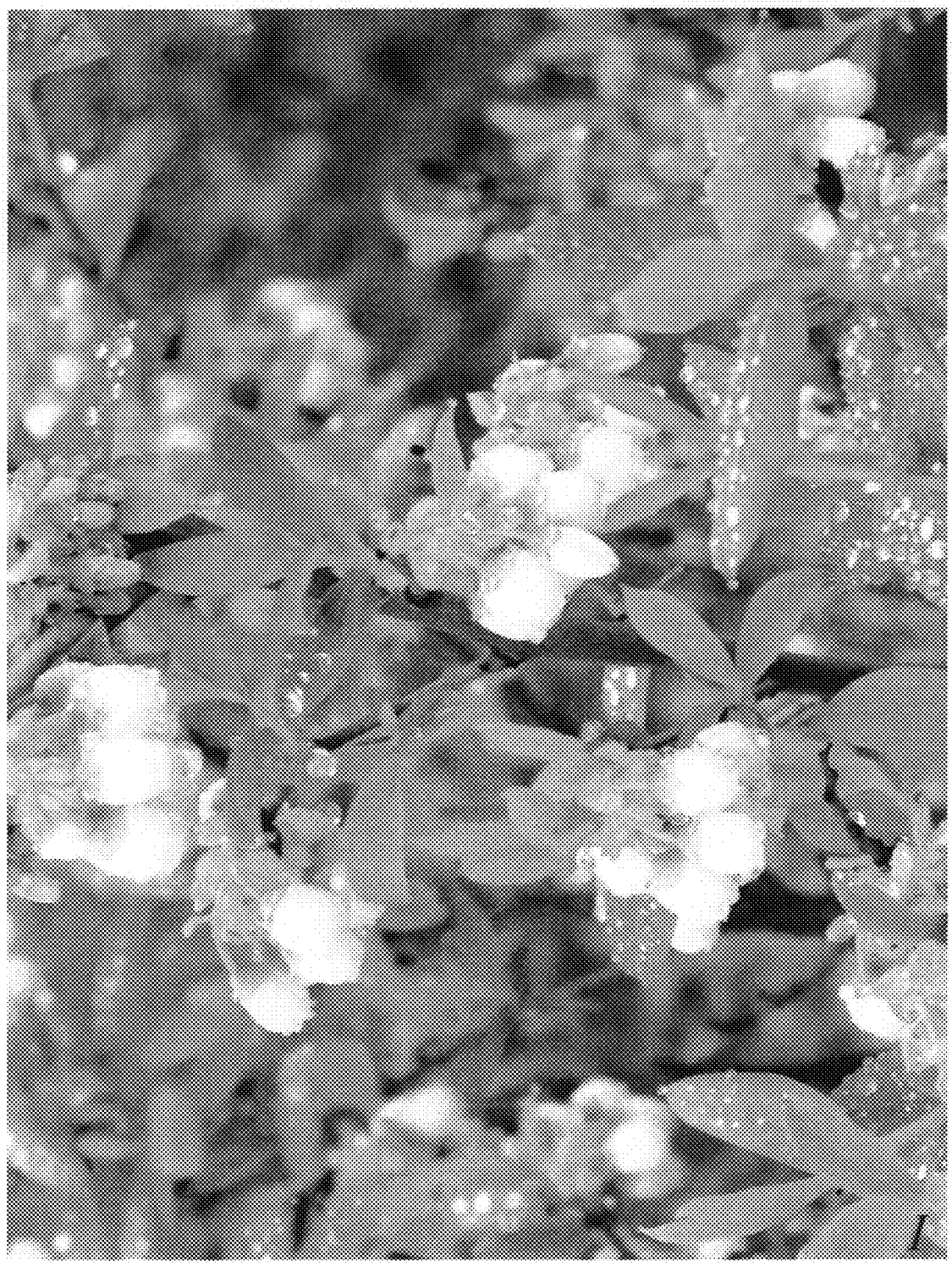
FIG. 2 is a second close-up photograph of 'BB06-343MI-16' taken in Mid-May, 2018, in Grand Junction, Mich., and shows opened and unopened flowers, including their shape and color, and the color of the peduncles and pedicels, and the shape and color of newly emerged leaves.
Figure 3:
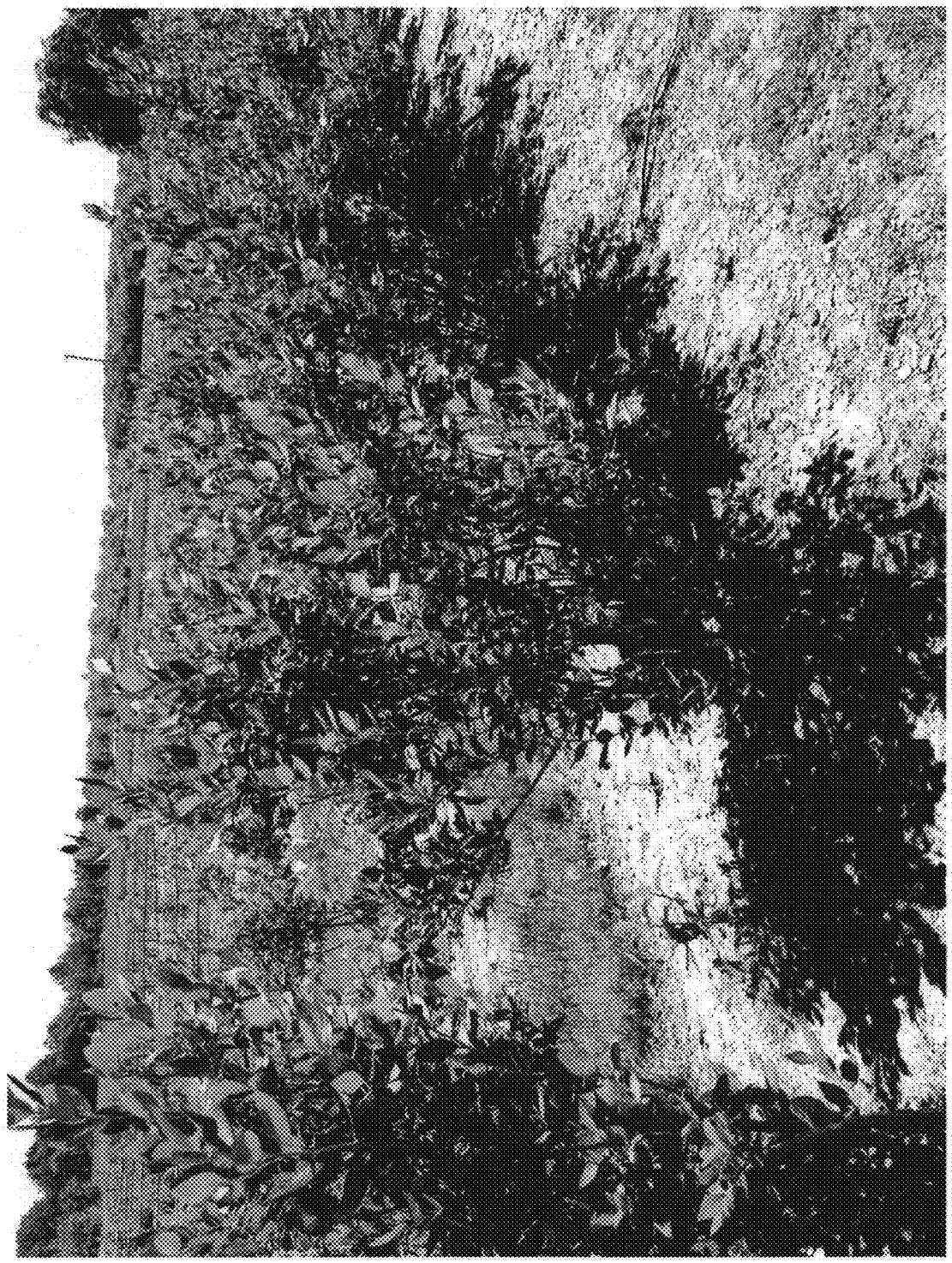
FIG. 3 is a photograph of 'BB06-343MI-16' taken in early July, 2018, in South Haven, Mich., and shows a 6-year-old bush showing the bush shape and crown size, and the mature cane number and structure, and the abundance of leaves and the fruit load.
Figure 4:
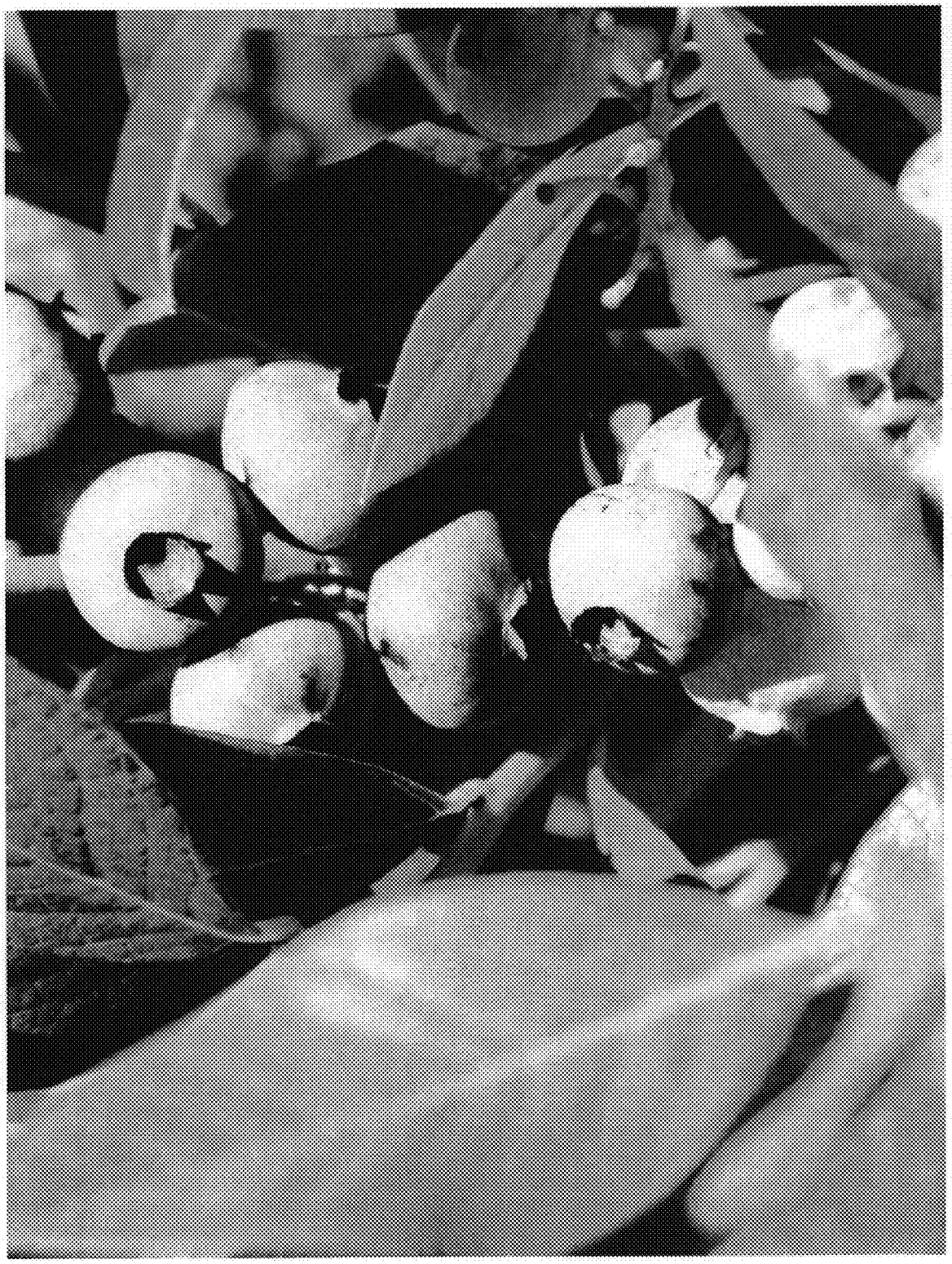
FIG. 4 is a close-up photograph of 'BB06-343MI-16' taken in early July, 2018, in South Haven, Mich., and shows ripe fruit including its shape, relative size and color, and the shape and size of the calyx.
Figure 5:
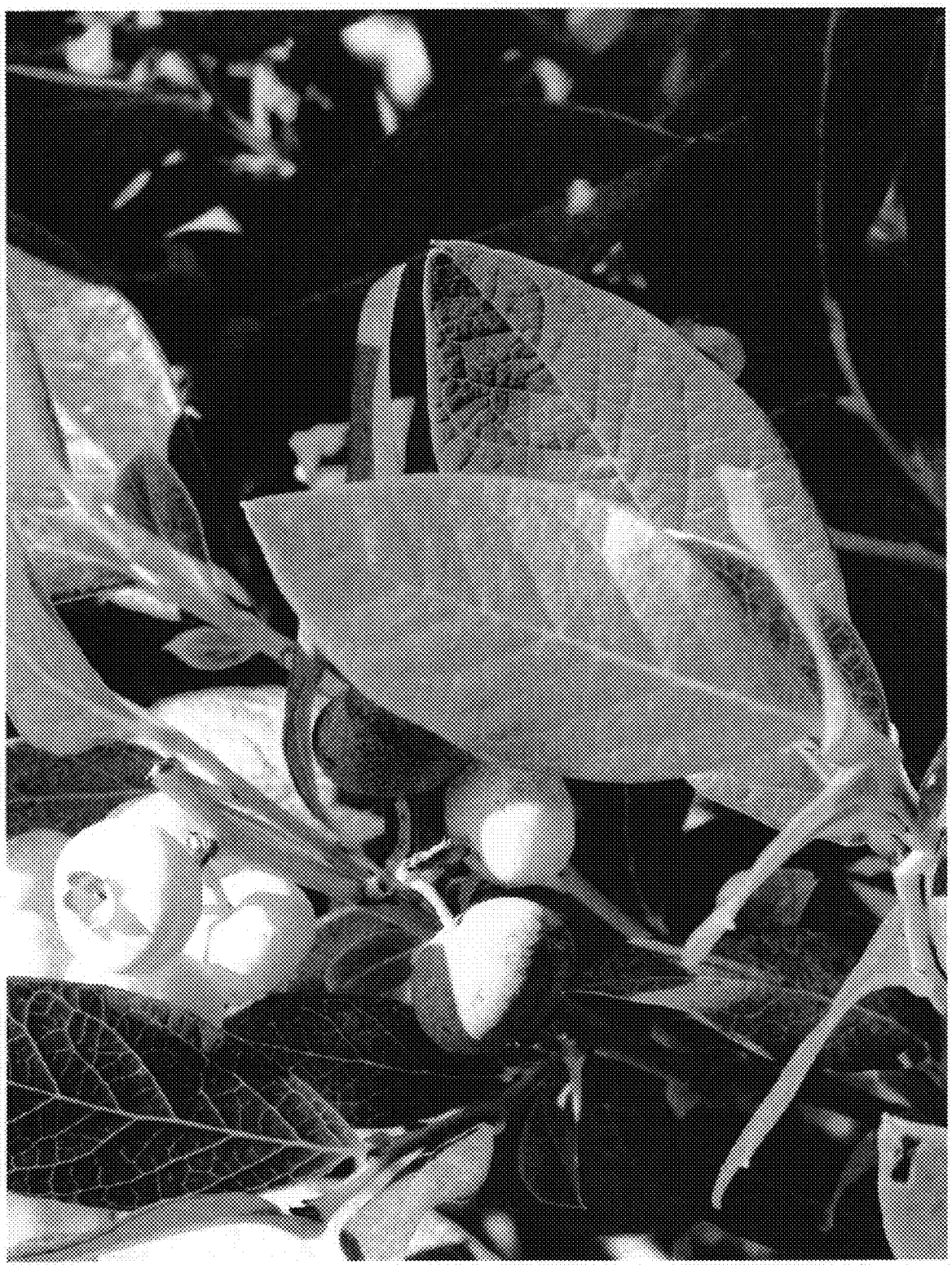
FIG. 5 is a close-up photograph of 'BB06-343MI-16' taken in early July, 2018, in South Haven, Mich., and shows the shape, size, venation and color of mature leaves, and the shape and color of ripe and unripe fruit, and the size and color of the pedicel.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely based on field observations made in 2018 of advanced trial plantings on mature 6-year-old bushes in Grand Junction, Mich., 7-year-old bushes in South Haven, Mich., and 4-year-old bushes in Hammonton, N.J. Laboratory analysis of fruit characteristics were done in Grand Junction, Mich. The bushes in the advanced trials were propagated from the original mother bush selected near Grand Junction, Mich., and all progeny have retained the characteristics of the original selection.

Cultivar Name: 'BB06-343MI-16'.

Classification:

Family: Ericaceae.

Botanical name: *Vaccinium corymbosum.*

Common name: Blueberry.

Parentage:

A. Female Parent

Name 'Draper' U.S. Plant Pat. No. 15,103 (child of 'Duke' (unpatented) x 'G 751' (unpatented)).

Differentiation: Compared to Draper, the bush habit of 'BB06-343MI-16' is more upright, the time of maturity is 10 days earlier, and the time of flowering is 10 days earlier. For 'BB06-343MI-16', the berry size and weight are less, and the berry is much firmer and has a flatter shape.

B. Male Parent

Name 'Cara's Choice' (unpatented) (child of 'G 144' x 'US 165', both unpatented).

Differentiation: Compared to 'Cara's Choice', 'BB06-343MI-16' has a slightly taller and more upright bush shape, the time of maturity is 7-10 days earlier and 'BB06-343MI-16' reaches 50% flowering 4 days earlier. 'BB06-343MI-16' has a lighter colored, larger, heavier, much firmer, and more acidic berry.

'BB06-343MI-16' originated from a cross of 'Draper' and 'Cara's Choice'. The cross was made in a greenhouse in Holland, Mich., in 2006. Emasculated flowers of 'Draper' were hand pollinated with pollen from 'Cara's Choice'. Seed was sown, germinated, and the plants were grown for 18 months in Grand Junction, Mich., and then planted in a seedling evaluation plot near Grand Junction, Mich., in 2008. The plant was evaluated for 4 years and first selected in July of 2011, based on its excellent fruit and morphological characteristics including maturity date, bush habit, berry quality, flavor, and storage ability. The bush was given the name 'BB06-343MI-16'. The 'BB06-343MI-16' bush was dug from the trial field in October 2012 and transplanted into a pot and placed in a virus-free screened greenhouse. Additional plants of 'BB06-343MI-16' have been propagated by softwood cuttings and tissue culture. Five and ten bush advanced trials were planted in Grand Junction, Mich., South Haven, Mich., Muskegon, Mich., and Hammonton, N.J. All of the plants propagated have retained the original characteristics.

Plants from vegetative softwood cuttings of 'BB06-343MI-16' were first propagated in 2011 in Grand Junction, Mich. and several times after. Micropropagation by tissue culture was first initiated in 2013. In all cases, the propagated plants from softwood cuttings and tissue culture have retained the original characteristics. The 'BB06-343MI-16' variety roots readily from softwood cuttings and tissue culture microshoots.

General Description: 'BB06-343MI-16' is a new and distinct high chill tetraploid Northern highbush blueberry (*Vaccinium*) variety consisting of primarily *V. corymbosum*, with a limited contribution of genes from *V. angustifolium* and *V. darrowii*. 'BB06-343MI-16' is a productive early season maturing variety. 'BB06-343MI-16' is characterized as having large fruit, medium blue in color, and is very firm with a very small and dry picking scar. The fruit is well exposed on a vigorous medium upright bush. Along with a small sized crown, a loose fruit cluster, concentrated ripening, and very firm fruit that is easily detachable, the variety displays characteristics suitable for mechanical harvest. 'BB06-343MI-16' is intended for areas that successfully grow high chill Northern highbush varieties. Ripe fruit are large, and average 2.2 grams/berry. The mean start date of flowering for 'BB06-343MI-16' in southern Michigan is April 28. Frost protection may be needed for successful pollination and fruit set. Winter chill requirement for successful flowering and leafing is at least 1000 hours below 7° C. Leaves emerge a few days before flowering commences. The mean 50% ripening date for 'BB06-343MI-16' is about July 3 in Grand Junction, Mich. The fruit shape is oblate in shape with a medium amount of waxy bloom that is rather persistent following handling. It has very good flavor, a balance of sweetness and acidity and is very juicy with a crunchy texture. It has a long and extended storage capability of 4 weeks or more in refrigeration with little decay.

References to color refer to The Pantone Book of Color, Eisemann and Herbert, Harry N. Abrams, Inc. Publishers, New York, ISBN 0-8109-3711-5, 1990.

Morphological characteristics reference: Plant Systematics, Jones and Luchsinger, 2 Ed., McGraw Hill, New York, ISBN 0-07-032796-3, 1986.

Device used to measure Soluble Solids (SS-Brix°), Titratable acidity (TA), pH: PAL-BX/Acid 7, Atago USA, Inc., Bellevue, Wash.

Firmness readings—BioWorks FirmTec2, Wamena, Kans.

Average size information:

*General description.*—Medium large bush, medium upright bush shape, 5-year-old bush averages 130 cm tall, 80 cm wide, height/width ratio=1.63.

*Growth.*—Very good growth and vigor, leafing is normal and abundant.

*Cold hardiness.*—Vegetative and flower buds −26° C., open flowers and fruit: −2° C.

Specific features of the variety:

Plant:

*Growth habit.*—Medium upright.

*Plant width.*—80 cm at mid-bush.

*Plant height.*—130 cm.

*Productivity.*—6-7 pounds per bush at maturity.

*Cold hardiness/tolerance.*—Vegetative and flower buds −26° C., open flowers and fruit: −2° C.

*Chilling requirement.*—1000 hours below 7° C.

*Canes.*—Moderately branched, 5 to 6 canes per bush, average length of 45 cm, range 41-52 cm in length, medium number of lateral branches, circular in shape, mature width 15 mm.

*Mature cane color.*—Pantone Gray Sand 13-1010.

*Mature cane texture.*—Rough.

*Fruiting wood.*—Smooth texture, immature winter color: Pantone Aurora Red 18-1550, immature summer color: Pantone Green Olive 17-0535.

*Internode length range.*—20-24 mm.

*Surface texture of new wood.*—Smooth.

*Time of beginning of leaf bud burst.*—April 19, Grand Junction, Mich.

*Time of beginning of flowering.*—April 28, Grand Junction, Mich.

*Date of 50% open flowers.*—May 12, Grand Junction, Mich.

*Time of beginning of fruit ripening.*—June 30, Grand Junction, Mich.

*Disease resistance/susceptibility.*—None claimed.

Foliage.

*Leaf color*.—Upper surface: Pantone Loden Green 18-0422, Lower surface: Pantone Mosstone 17-0525.

*Leaf arrangement*.—Simple Alternate.

*Leaf margins*.—Entire.

*Leaf venation*.—Pinnate.

*Leaf shape*.—Elliptic.

*Leaf apices*.—Acute.

*Leaf bases*.—Acute.

*Vein and petiole coloration*.—Pantone Spinach Green 16-0439.

*Petiole length*.—4 mm.

*Petiole diameter*.—0.75 mm.

*Evergreen*.—No.

Leaf dimensions:

*Overall shape*.—Elliptic.

*Length*.—Range 62-75 mm, average 68 mm.

*Width*.—Range 27-32 mm, average 30 mm.

*Leaf margins*.—Entire, 3-4 nectaries visible with microscope (30X) near basal end underside.

*Leaf surface*.—No visible pubescence.

Flower buds:

*Shape*.—Elliptic.

*Length*.—6 mm.

*Width*.—5 mm.

*Color*.—Pantone Deep Sea Coral 18-1649.

Flower:

*Flower shape*.—Urceolate.

*Flower bud number*.—Medium high.

*Flowers per cluster*.—Average 8 per cluster.

*Flower fragrance*.—Light floral.

*Corolla color*.—Pantone Turtle Dove 12-5202.

*Corolla length*.—8 mm.

*Corolla width*.—4 mm.

*Corolla aperture width*.—5 mm.

*Corolla texture*.—Smooth.

*Flower peduncle length*.—8 mm.

*Peduncle diameter*.—1 mm.

*Peduncle texture*.—Slightly rough.

*Peduncle color*.—Pantone Spinach Green 16-0439.

*Flower pedicel length*.—4 mm.

*Pedicel diameter*.—0.75 mm.

*Pedicel texture*.—Smooth.

*Pedicel color*.—Pantone Spinach Green 16-0439.

*Calyx* (*with sepals*).—2 mm.

*Calyx color*.—Pantone Spinach Green 16-0439.

*Stamen length*.—6 mm.

*Number per flower*.—10.

*Filament color*.—Pantone Raw Sienna 17-1436.

*Style*.—8 mm in length.

*Style color*.—Pantone Spinach Green 16-0439.

*Pistil*.—6 mm top of ovary to stigma tip, even with top of corolla.

*Ovary color*.—Pantone Spinach Green 16-0439.

*Anther length*.—3 mm.

*Number*.—10.

*Color*.—Pantone Raw Sienna 17-1436.

Pollen:

*Abundance*.—Moderately abundant.

*Color*.—Pantone Pastel Yellow 11-0616.

Fruit:

*Date of* 50% *maturity*.—July 3, Grand Junction, Mich.

*Duration of ripening*.—Approximately 18 days.

*Yield*.—6-7 pounds per bush at maturity.

*Cluster density*.—Loose.

*Immature fruit color*.—Pantone 16-0439 Spinach Green.

*Berry color with wax*.—Pantone Lead 17-4408.

*Berry color with wax removed*.—Pantone Majolica Blue 19-4125.

*Berry flesh color*.—Pantone Frozen Dew 13-0513.

*Berry surface wax abundance*.—Medium, medium persistent.

*Berry weight*.—Average 2.2 grams/berry.

*Berry size diameter*.—18 mm.

*Berry height*.—12 mm.

*Berry shape*.—Oblate.

*Average number of fruit per cluster*.—Average 7-8.

*Average weight of fruit per cluster*.—Average 16.5 grams.

*Detachment force*.—Easy.

*Self-fruitfulness*.—Very good.

*Fruit stem scar*.—Small, dry 1 mm diameter.

*Calyx shape*.—5 point.

*Calyx diameter*.—6 mm.

*Calyx depth*.—2 mm.

*Berry firmness*.—Very firm, FirmTec: 230 g/mm$^2$.

*Berry sweetness*.—Medium high, Brix°=13.5.

*Berry acidity*.—Medium high, titratable acidity=0.91.

*Berry flavor and texture*.—Balanced flavor of sweetness and acidity, juicy and very crunchy texture.

*Storage ability*.—Excellent.

*Suitability for mechanical harvesting*.—A small bush crown, a medium upright bush shape, very firm fruit and easy detachment are desirable for mechanical harvest.

*Uses*.—Fresh market, processing into jams, purees, and yogurt.

Seed:

*Seed abundance in fruit*.—Medium abundant.

*Seed color*.—Pantone Baked Clay 18-1441.

*Seed dry weight*.—NA.

*Seed size*.—0.75 mm length, 0.5 mm width.

Possible typical market uses: Fresh market, processing into jams, purees, and yogurt.

What is claimed is:

1. A new and distinct cultivar of Blueberry plant named 'BB06-343MI-16' as described and shown herein.

* * * * *